United States Patent
Herrlein et al.

(10) Patent No.: US 9,563,942 B2
(45) Date of Patent: Feb. 7, 2017

(54) METHOD AND APPARATUS FOR CREATING IMAGES OF FIBROUS STRUCTURES

(71) Applicant: Noxell Corporation, Hunt Valley, MD (US)

(72) Inventors: Mathias Herrlein, Kronberg (DE); Thomas Hirn, Weiterstadt (DE); Knut Meinert, Lampertheim (DE); Hartmut Schmidt, Pahl (DE); Arno Zinke, Bonn (DE)

(73) Assignee: NOXELL CORPORATION, Hunt Valley, MD (US)

( * ) Notice: Subject to any disclaimer, the term of this patent is extended or adjusted under 35 U.S.C. 154(b) by 130 days.

(21) Appl. No.: 14/488,966

(22) Filed: Sep. 17, 2014

(65) Prior Publication Data

US 2015/0077533 A1   Mar. 19, 2015

(30) Foreign Application Priority Data

Sep. 17, 2013   (EP) ..................... 13184818

(51) Int. Cl.
| | |
|---|---|
| *H04N 9/47* | (2006.01) |
| *G06T 5/00* | (2006.01) |
| *H04N 5/225* | (2006.01) |
| *G01N 21/47* | (2006.01) |
| *G01N 21/03* | (2006.01) |

(52) U.S. Cl.
CPC .......... *G06T 5/005* (2013.01); *G01N 21/4738* (2013.01); *H04N 5/2256* (2013.01); *G01N 2021/0339* (2013.01); *G01N 2021/4764* (2013.01); *G01N 2201/0633* (2013.01); *G06T 2207/10024* (2013.01)

(58) Field of Classification Search
None
See application file for complete search history.

(56) References Cited

U.S. PATENT DOCUMENTS

| | | | | |
|---|---|---|---|---|
| 2002/0065469 A1* | 5/2002 | Hsu | ...................... | A61B 5/0059 600/478 |
| 2008/0055591 A1* | 3/2008 | Walton | ............... | G01N 21/8901 356/237.1 |

OTHER PUBLICATIONS

Lu; Optical Properties (bidirectional reflectance distribution function) of shot fabric, Applied Optics, vol. 39, No. 31, p. 5785, Publication date: Nov. 1, 2000.
Zinke; A Practical Approach for Photometric Acquisition of Hair Color, ACM Transactions on Graphics, vol. 28, No. 5, Article 165, Publication date: Dec. 2009.
Zinke; Light Scattering from Filaments, IEEE Transactions on Vizualization and Computer Graphics.
International Search Report and Written Opinion, PCT/US2014/054872, date of mailing Nov. 27, 2014.

* cited by examiner

*Primary Examiner* — Chikaodili E Anyikire
(74) *Attorney, Agent, or Firm* — Schwegmann Lundberg & Woessner, P.A.

(57) ABSTRACT

Apparatus and method for rendering an image of a fibrous material. The method includes providing parametric fibrous material optical properties derived from actual material fiber samples via the apparatus; providing a parametric virtual light environment; providing a virtual fibrous material array; and rendering an image of the virtual fibrous material array according to the interaction of the parametric fibrous material properties and the parametric virtual light environment.

6 Claims, 4 Drawing Sheets

METHOD AND APPARATUS FOR CREATING IMAGES OF FIBROUS STRUCTURES

FIELD OF THE INVENTION

The invention relates to apparatus and methods for creating images of fibrous structures. The inventions relates particularly to apparatus for capturing information related to actual fibrous structures and methods for utilizing that information to create images of virtual fibrous structures.

BACKGROUND OF THE INVENTION

Creating images of virtual fibrous structures, such as hair, is known in the art. Efforts in this area typically focus upon the creation of images having a desired appearance, regardless of any link between the created appearance and an actual fibrous structure. What is necessary is a method and apparatus for the creation of fibrous structure images which are optically and/or color correct.

SUMMARY OF THE INVENTION

In one embodiment, an apparatus for determining material optical properties includes: a material holder comprising a curvilinear surface; a collimated light source disposed in alignment with a surface normal of the curvilinear surface, to illuminate the material holder; and an image capture element aligned with the collimated light source and the surface normal of the curvilinear surface of the material holder. An angular offset between an axis of the collimated light source and an axis of the image capture element, each in a plane of the surface normal of the curvilinear surface of the material holder, is less than about 5 degrees.

In one embodiment, a method for defining an optical fingerprint for a fibrous material includes: disposing a sample of the fibrous structure upon a material holder comprising a curvilinear surface; illuminating the disposed sample with a collimated light source disposed in alignment with a surface normal of the curvilinear surface, to illuminate the material holder; capturing at least one digital image of the disposed fibrous sample using an image capture element aligned with the collimated light source and the surface normal of the curvilinear surface of the material holder, wherein an angular offset between an axis of the collimated light source and an axis of the image capture element, each in a plane of the surface normal of the curvilinear surface of the material holder, is less than about 5 degrees; correcting the captured image according to the angular offset between the collimated light source and the image capture element; replacing erroneous pixels in the captured image with non-erroneous pixels; and defining parameters according to an optimized fit between a modeled image of fibers and the captured image of fibers. The replacement of erroneous pixels or smoothing step reduces the effect of misaligned fibers which protrude from the surface of the fiber holder leading to erroneous pixels.

In one embodiment, a method includes providing parametric fibrous material optical properties derived from actual material fiber samples via the apparatus; providing a parametric virtual light environment; providing a virtual fibrous material array; and rendering an image of the virtual fibrous material array according to the interaction of the parametric fibrous material properties and the parametric virtual light environment.

DETAILED DESCRIPTION OF THE INVENTION

As used herein the term optically correct refers to an image which accurately portrays the interaction of visible electromagnetic radiation with a fibrous structure of particular optical properties.

As used herein the term color correct refers to an image which accurately portrays a fibrous structure of particular optical properties illuminated by a visible electromagnetic radiation source having a particular emissive spectrum.

As used herein the term fibrous structure refers to any structure comprised of discrete strands or fibers. These fibers may be artificial or natural fibers. In particular the term may be used to refer to an array of strands of keratinous materials. Keratinous fibers may be selected from wool, fur, silk, hair and mixtures thereof; preferably from mammalian hair; more preferably from human hair. Hair may be living hair i.e. on a living body or non-living hair i.e. in a wig, hairpiece or other aggregation of non-living keratinous fibers. Hair may be from Caucasian, Asian, African, Afro-Caribbean origins or combinations of these ethnic types. Hair may be selected from non-treated hair (i.e. virgin hair), treated hair and mixtures thereof. Treated hair may be selected from artificially-colored hair, bleached hair, permanently-waved hair, and mixtures thereof.

These fibers may have an average diameter from about 10 to about 200 microns, preferably from about 30 to about 150 microns, more preferably about 50 to about 120 microns.

Figure 1:
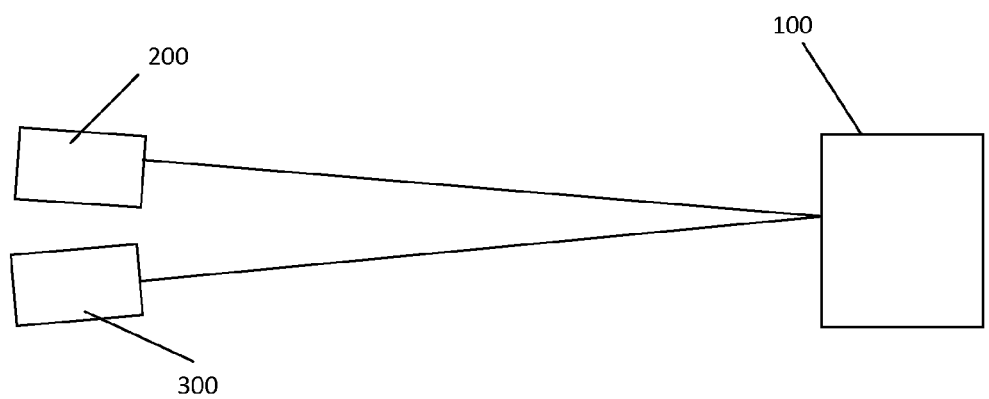
FIG. 1 provides a schematic plan view of an apparatus according to one embodiment of the invention.
Figure 2:
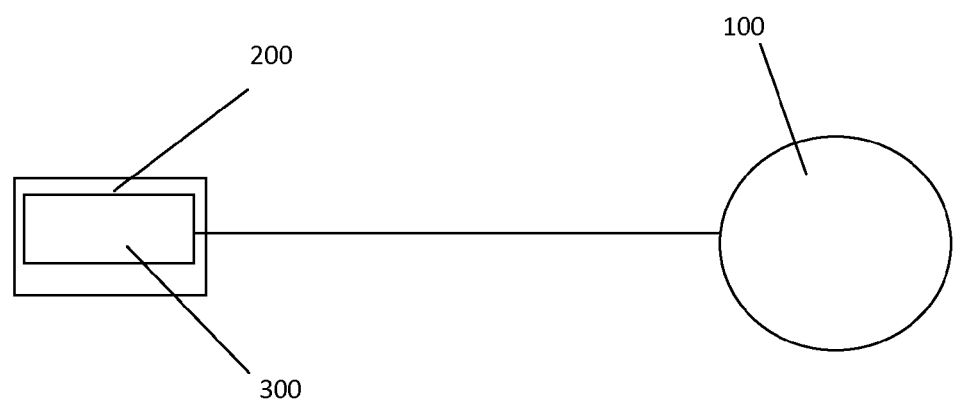
FIG. 2 provides a schematic side view of an apparatus according to one embodiment of the invention.

In one embodiment, illustrated in FIGS. 1 and 2, an apparatus for determining material optical properties comprises: a material holder comprising a curvilinear surface 100; a collimated light source 200 disposed in alignment with a surface normal of the curvilinear surface 100. The light source provided illuminates the material holder 100. The apparatus further comprises an image capture element 300 aligned with the collimated light source 200 and the surface normal of the curvilinear surface of the material holder 100, an angular offset between an axis of the collimated light source 200 and an axis of the image capture element 300, each in the same plane of a surface normal of the curvilinear surface of the material holder 100, less than about 5 degrees. In one embodiment, the offset between the two axes is less than about 3 degrees. In one embodiment, either the image capture element or the illumination source is disposed such that its axis is normal to the curvilinear surface of the material holder, with the other axis disposed at an angular offset as described above. Alternatively, each of the two axes may be disposed about half of the maximum angular offset from being normal to the curvilinear surface of the material holder. As an example, each of the two axes may be disposed about 2.5 degrees from normal to the curvilinear surface. The divergence angle of the collimated light may be less than about 0.5 degrees. The luminance of the light source in the area where the target material is mounted should not vary by more than 5% of the average luminance in this area.

In one embodiment, the image capture element and illumination source are each aligned to within about 5 degrees, preferably within about 1 degree, more preferably within about 0.2 degrees, of an imaginary plane including a surface normal of the curvilinear surface of the material holder.

Figure 3:
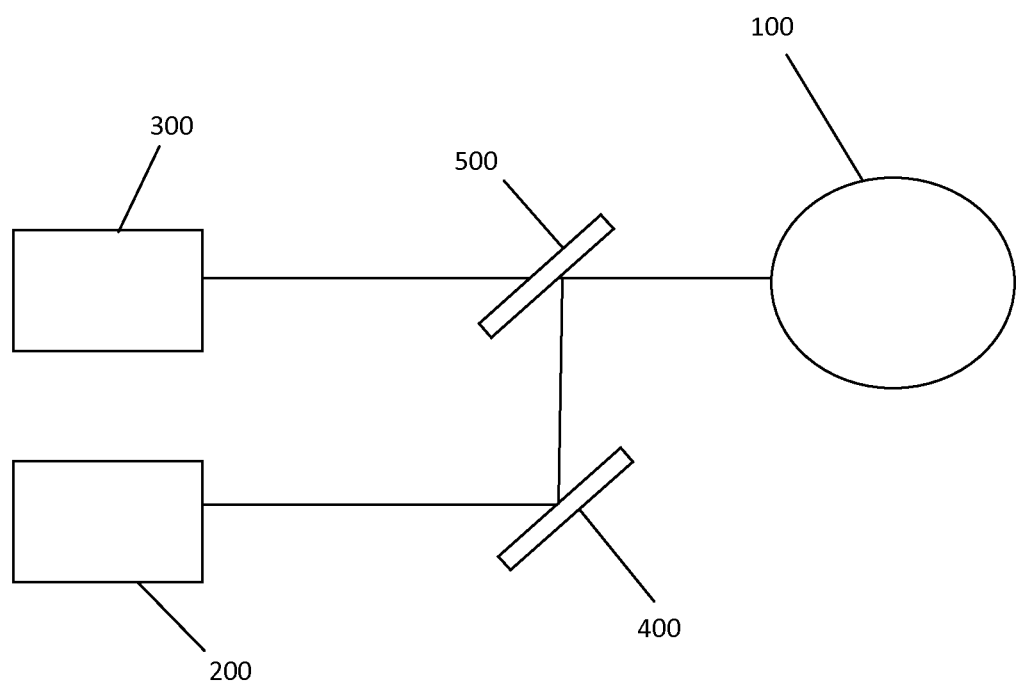
FIG. 3 provides a schematic view of an apparatus according to one embodiment of the invention.

FIG. 3 illustrate an embodiment wherein the collimated light source 200 is disposed with its axis parallel to, but not otherwise aligned with, the axis of the image capture element 300. Surface mirror 400 and half silvered mirror 500 are disposed to bring the output of the collimated light source 200 into alignment with the axis of the image capture element and to illuminate the image capture surface 100. A beam splitter may be substituted for the half silvered mirror 500.

Figure 4:
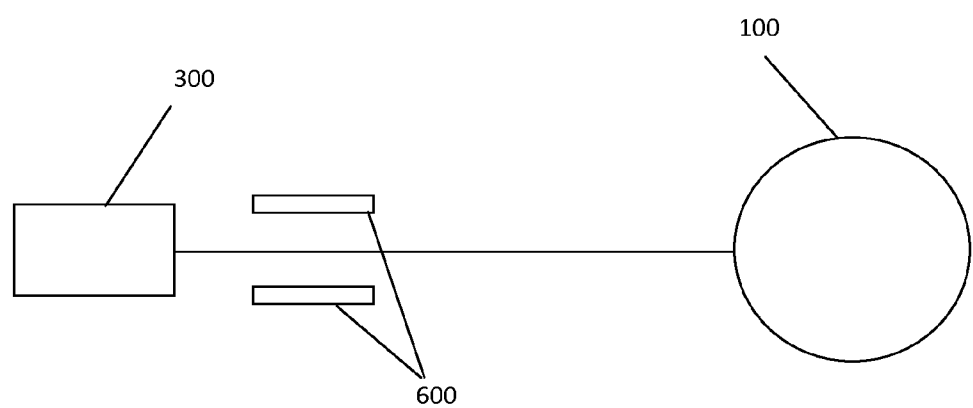
FIG. 4 provides a schematic view of an apparatus according to one embodiment of the invention.

FIG. 4 illustrates an embodiment wherein a ring light 600 is disposed such that the axis of illumination of the ring light 600 is aligned with the axis of the image capture element 300.

In one embodiment, a Xenon High Pressure light source may be used to illuminate the material and material holder. The 150 W Xenon arc lamp Model: 6255 Oriel Instruments available from LOT Quantum Design GmbH (Germany) is an exemplary light source. The light source may be a $D_{55}$ simulator. $D_{55}$ corresponds roughly to midday sun light in Western Europe/Northern Europe; hence it is also called a daylight illuminant.

The material holder may have a cylindrical cross section or other cross section comprising at least a curvilinear portion disposed facing the illumination source and the image capture element. The material holder may be fabricated from any suitable material including wood, metal, glass, polymers, or composite materials. The material holder may comprise a comb or other fiber separating element to enable the material sample to be arrayed upon the material holder with the fibers separated and aligned upon the curvilinear surface.

The image capture element may comprise a high dynamic range digital camera. An exemplary image capture element, a camera, is the TXG50c available from the Baumer Group, of Frauenfeld, Switzerland, and having a dynamic range of 12 bits for each of the Red, Green and Blue channels is an exemplary image capture element. A digital camera of lower dynamic range may be used as the image capture element providing that multiple images at different exposures are captured and combined.

The sample of fibrous structure may comprise fibrous structures as defined hereinabove. This sample may comprise from about 2 to about 10000, preferably from about 10 to about 5000, more preferably from about 100 to about 2000, fibrous structures.

In practice, a sample of fibrous material, such as hair, is disposed in an aligned array upon the curvilinear surface of the material holder. The arrayed fibers may be disposed in multiple layers upon the surface or in a single layer. The aligned disposition may be made easier through the utilization of a fiber separating element. The disposed array of fibers may be illuminated using the collimated $D_{55}$ illumination source. The 6255 Xenon Lamp, available from Oriel Instruments, available from LOT Quantum Design GmbH (Germany), is an exemplary illumination source. At least one digital image of the illuminated fiber sample is captured for analysis, though more than one image may be captured. In one embodiment, the captured digital image is a high resolution image. The angular relationship between the image capture element, the illumination source and the material holder may be as described above.

The capture image may be analyzed using software from GfaR, available from Dr. Arno Zinke, to determine values for intensity of RGB signals along columns of the image.

The captured image may be corrected to reduce the effects produced by the angular offset between the illumination source and the image capture element. In one embodiment, this image correction may be accomplished utilizing the GfaR software developed by Dr. Arno Zinke, GfaR, GmbH, Bonn, Germany.

The image may be smoothed by calculating an average value for each row of pixels in the image and subsequently altering the value of each pixel as necessary to reduce the difference between the value of the particular pixel and the average value for the row of pixels.

Optical fingerprint parameters (OFP) including: Absorption red (radius (hair fiber)^-1), Absorption green (radius (hair fiber)^-1), Absorption blue (radius (hair fiber)^-1), long Shift R (Degrees), long Shift TT (Degrees), long Shift TRT (Degree), long Width R (Degrees), long Width TT (Degrees), long Width TRT (Degrees), Scale R (no units), diffuse Fraction (no units), diffuse Reflectance red (no units), diffuse Reflectance green (no units), and diffuse Reflectance blue (no units), are defined for the image. As used in the previous sentence, the term "R" means "Reflection (on the outer surface)", "TT" means "2×Transmission (no reflection back towards the light source)" and "TRT" means "Transmission, Reflection, Transmission (reflection on the inner back side)". The values of the parameters are calculated using algorithms developed by Dr. Zinke, to estimate a bi-directional reflectance distribution function (BRDF) and to determine a bi-directional curve scattering distribution function, (BCSDF) using the GfaR software.

The calculation is performed iteratively to reduce the error between an image rendered virtually using the parameters and the initial image of the fibrous material to a minimum value.

Images of virtual fibrous materials may subsequently be created using the calculated OFP by using the OFP values together with a virtual model of a fibrous structure, a virtual illumination source of a particular luminosity and spectrum, arranged in a particular location relative to the virtual model and calculating the appearance of the fibrous structure according to the interaction of the parametric fibrous material properties and the parametric virtual light environment. The creation of the images may be accomplished via monte carlo path tracing and may take into consideration the definition of the light source in terms of its distance from the object, the size and distribution of the luminance and the angular distribution of the outgoing rays, the definition of the position and orientation of the hair model, and the definition and position and orientation of the camera.

OFP values in following ranges have been found to yield acceptable representations of fibrous structures when compared to actual images of underlying fibrous structures: Absorption r 0.00805 to 2.96; Absorption g 0.018365 to 2.9613, Absorption b 0.031964 to 2.984, long Shift R (−8.3837) to (−0.9615), long Shift TT (−0.33319) to (3.8045), long Shift TRT (−0.99956) to 11.4136, long Width R 1.4976 to 12.4241, long Width TT 1.6076 to 15.3835, long Width TRT 4.1421 to 35.5172, Scale R 0.60002 to 0.99999, diffuse Fraction 0.00225 to 0.28391, diffuse Reflectance r 0.20935 to 1.124, diffuse Reflectance g 0.083714 to 1.0391, and diffuse Reflectance b 0.013692 to 1.0381.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for determining material optical properties, the apparatus comprising:
   a. a material holder comprising a curvilinear surface;
   b. a collimated light source disposed in alignment with a surface normal of the curvilinear surface, to illuminate the material holder, wherein the collimated light source has an output; and
   c. an image capture element aligned with the collimated light source and the surface normal of the curvilinear surface of the material holder;
   wherein an angular offset between an axis of the collimated light source and an axis of the image capture element, each in a plane of the surface normal of the curvilinear surface of the material holder, is less than about 5 degrees; and
   wherein a surface mirror and a half silvered mirror are disposed to bring the output of the collimated light source into alignment with the axis of the image capture element and to illuminate an image capture surface.

2. The apparatus according to claim 1 wherein the material holder further comprises a fiber separator.

3. The apparatus according to claim 1 wherein the angular offset is less than about 3 degrees.

4. The apparatus according to claim 1 wherein the collimated light source is aligned within about 0.2 degrees of the surface normal of the curvilinear surface of the material holder.

5. The apparatus according to claim 1 wherein the image capture element is aligned within about 0.2 degrees of the surface normal of the curvilinear surface of the material holder.

6. The apparatus according to claim 1 wherein at least one of the axis of the collimated light source and the axis of the image capture element is aligned to within about 2.5 degree to an axis normal to the curvilinear surface of the material holder.

* * * * *

UNITED STATES PATENT AND TRADEMARK OFFICE
CERTIFICATE OF CORRECTION

PATENT NO. : 9,563,942 B2
APPLICATION NO. : 14/488966
DATED : February 7, 2017
INVENTOR(S) : Herrlein et al.

It is certified that error appears in the above-identified patent and that said Letters Patent is hereby corrected as shown below:

On the Title Page

In item (30), in "Foreign Application Priority Data", in Column 1, Line 1, delete "13184818" and insert --13184818.6-- therefor In Column 2, under "Other Publications", Line 8, delete "Vizualization" and insert --Visualization-- therefor Signed and Sealed this
Seventeenth Day of April, 2018

Andrei Iancu
*Director of the United States Patent and Trademark Office*